United States Patent
Eibergen

(10) Patent No.: US 10,150,944 B2
(45) Date of Patent: Dec. 11, 2018

(54) METHOD FOR DECREASING THE CONCENTRATION OF SULFATE REDUCING BACTERIA IN AN AQUEOUS SYSTEM

(71) Applicant: Dow Global Technologies LLC, Midland, MI (US)

(72) Inventor: Nora R. Eibergen, Collegeville, PA (US)

(73) Assignee: DOW GLOBAL TECHNOLOGIES LLC, Midland, MI (US)

(*) Notice: Subject to any disclaimer, the term of this patent is extended or adjusted under 35 U.S.C. 154(b) by 28 days.

(21) Appl. No.: 15/381,224

(22) Filed: Dec. 16, 2016

(65) Prior Publication Data
US 2017/0191138 A1    Jul. 6, 2017

Related U.S. Application Data

(60) Provisional application No. 62/272,842, filed on Dec. 30, 2015.

(51) Int. Cl.
| | | |
|---|---|---|
| *C12N 1/20* | (2006.01) | |
| *C09K 8/524* | (2006.01) | |
| *A01N 63/00* | (2006.01) | |
| *C02F 3/34* | (2006.01) | |

(52) U.S. Cl.
CPC .............. *C12N 1/20* (2013.01); *A01N 63/00* (2013.01); *C02F 3/34* (2013.01); *C09K 8/524* (2013.01); *C02F 3/348* (2013.01); *C02F 2307/14* (2013.01)

(58) Field of Classification Search
None
See application file for complete search history.

(56) References Cited

U.S. PATENT DOCUMENTS

| | | |
|---|---|---|
| 5,405,531 A | 4/1995 | Hitzman et al. |
| 6,281,002 B1 | 8/2001 | Moller-Bremer |
| 7,060,486 B2 | 6/2006 | Wood et al. |
| 9,096,449 B1 | 8/2015 | Conway |

OTHER PUBLICATIONS

Fang et al. 2012 (*Brassicibacter mesophilus* gen. nov., sp. nov., a strictly anaerobic bacterium isolated from food industry wastewater; International Journal of Systematic and Evolutionary Microbiology; 62: 3018-3023). (Year: 2012).*

Liu et al. 2008 (Abundance and diversity of sulphate-reducing bacteria within a crude oil gathering and transferring system in China; Annals of Microbiology 58(4): 611-615) (Year: 2008).*

Karnachuk et al. 2006 (Distribution, Diversity, and Activity of Sulfate-Reducing Bacteria in the water column in Gek-Gel Lake, Azerbaijan; Microbiology 75(1):82-89) (Year: 2006).*

* cited by examiner

Primary Examiner — Mary Maille Lyons
(74) Attorney, Agent, or Firm — Tifani M. Edwards

(57) ABSTRACT

The invention relates to a method of decreasing the concentration of sulfide reducing bacteria in an aqueous system, particularly in an aqueous system used in oil-field applications.

8 Claims, No Drawings
Specification includes a Sequence Listing.

METHOD FOR DECREASING THE CONCENTRATION OF SULFATE REDUCING BACTERIA IN AN AQUEOUS SYSTEM

INCORPORATION-BY-REFERENCE OF MATERIAL SUBMITTED IN ELECTRONIC FORM

Applicant hereby incorporates by reference the Sequence Listing material filed in electronic form herewith. This file is labeled "78774-US-NP_ST25.txt", created on Feb. 10, 2017, and is of a size of 1 kB.

The invention relates to a method of decreasing the concentration of sulfide reducing bacteria in an aqueous system, particularly in an aqueous system used in oil-field applications. The invention further relates to a method of using an aqueous system which has a reduced amount of sulfate reducing bacteria in enhanced oil recovery.

Sulfate-reducing bacteria (SRB) are notorious for their detrimental effects on the vast infrastructure required to produce and transport oil and gas. These organisms, known for growing in both planktonic and sessile communities, are some of the major contributors to reservoir souring, microbially influenced corrosion (MIC) of equipment and other mild steel components, and biofilm-induced clogging and restriction of flow. The negative impact of SRB on both oil production costs and product quality has made these organisms attractive targets for advanced microbial control strategies.

Within the SRB class, those bacteria in the genera *Desulfovibrio* have been demonstrated to be prevalent in oil and gas applications. In particular, *Desulfovibrio vulgaris* (*D. vulgaris*) forms robust biofilms that are able to induce pitting corrosion in mild steel. U.S. Pat. No. 7,060,486 discloses that the addition of bacteria which secrete antimicrobial agents to a system containing SRB may inhibit the growth of SRB in aqueous systems. Although biocidal efficacy has been positively demonstrated against SRB, a demand exists for biocide alternatives that are less toxic and more sustainable.

The present invention solves the problem of the art by providing an approach to controlling the growth of *D. vulgaris*. This approach involves the application of *Brassicibacter mesophilus* to environments contaminated with *D. vulgaris*.

In accordance with the present invention there is provided method of decreasing the concentration of sulfate reducing bacteria in an aqueous system comprising the steps of:

i. adding *Brassicibacter mesophilus* to an aqueous system; and ii. contacting the *Brassicibacter mesophilus* with sulfate reducing bacteria in the aqueous system. The present invention also provides a method of recovering oil from oil wells comprising injecting an aqueous system which has been treated in accordance with the aforementioned method of decreasing the concentration of sulfate reducing bacteria, into a subterranean oil-bearing formation.

In the present invention *Brassicibacter mesophilus*, in an amount sufficient to decrease the concentration of sulfate reducing bacteria, is added to an aqueous system. Generally, *Brassicibacter mesophilus* in any amount, even small amounts, will have some effect on reducing the concentration of sulfate reducing bacteria. The aqueous system may be any potable, wastewater, or industrial aqueous system known to those of skill in the art.

The *Brassicibacter mesophilus* (*B. mesophilus*) is then brought into contact with sulfate reducing bacteria. This contact occurs when *B. mesophilus* is added to an aqueous system comprising SRB. Whether the SRB is already present in the aqueous system prior to addition of the *B. mesophilus* or it is subsequently added after the *B. mesophilus* is of no consequence. It is envisioned that the contact may be a continuous process or may be a one-time batch process.

The sulfate reducing bacteria is of the genera *Desulfovibrio*, and more specifically is *Desulfovibrio vulgaris*. As function of time, the number of SRB cells decreases as the number of *Brassicibacter mesophilus* cells increases.

This invention further provides a method of recovering oil from oil wells comprising injecting an aqueous system which has been treated in accordance with the aforementioned method, into a subterranean oil-bearing formation and may be used anywhere sulfate-reducing bacteria are causing or have caused or have the potential for causing hydrogen sulfide generation. This invention uses bacterial strain *Brassicibacter mesophilus* as a bioremediation strategy for controlling the growth of *Desulfovibrio vulgaris*. *Desulfovibrio vulgaris* is a sulfate reducing bacterium that has been found in gas pipelines, subsurface metal tanks, sediments, and off-shore oil production facilities. The production of hydrogen sulfide by this bacterium causes petroleum souring and metal corrosion. Control of this organism is currently limited to treatment with biocides. *Brassicibacter mesophilus* is an anaerobic organism that was isolated from food industry wastewater and has been shown to reduce the population of *Desulfovibrio vulgaris* in co-culture. For example, when a stationary-phase culture of *Desulfovibrio vulgaris* is inoculated with *Brassicibacter mesophilus* and grown for 14 days, the *Desulfovibrio vulgaris* culture is decreased to 27% of its population observed in the same culture after 3 days incubation with *Brassicibacter mesophilus*. This is compared to a 14 day *Desulfovibrio vulgaris* culture that is not inoculated with *Brassicibacter mesophilus*. The population of this culture after 14 days incubation is 162% of that observed for the same culture after only 3 days of incubation. The application of *Brassicibacter mesophilus* represents a more sustainable strategy for controlling the growth of *Desulfovibrio vulgaris* than the currently employed biocidal strategies.

The present invention is demonstrated by the following Examples, but it is to be understood that the Examples are for exemplary purposes only and does not serve to limit the invention.

EXAMPLES

Microorganisms and Growth Conditions

*Desulfovibrio vulgaris* (ATCC 29479) was purchased from ATCC (Manassus, Va.) and *Desulfovibrio longus* (DSMZ 6739) was purchased from DSMZ (Braunschweig, Germany). *Desulfovibrio alaskensis* was initially purchased from ATCC as *Desulfovibrio longus* (ATCC 51456) at the Springhouse Dow facility; however, the identity of this isolate was later confirmed to be *Desulfovibrio alaskensis* by sequencing of the 16S rRNA gene. *Brassicibacter mesophilus* was isolated from a contaminated flow loop experimental setup by collecting planktonic culture from each loop after 4 weeks of growth. The collected culture was subsequently analyzed by Denaturing Gradient Gel Electrophoresis (DGGE; procedure described below), and *Brassicibacter mesophilus* was the only organism detected in the cultures. Spent media was prepared by passing the loop cultures through 0.2 μM filters. After filtration, no growth was observed in spent media samples for up to 2 months.

All cultures were grown under anaerobic conditions at 30° C. in Modified Baar's (MB) media without salt. One liter of this media contains the following: 2.0 g $MgSO_4$, 5.0 g Sodium citrate, 1.0 g $CaSO_4 \times H_2O$, 1.0 g $NH_4Cl$, 0.5 g $K_2HPO_4$, 3.5 g Sodium lactate, 1.0 g Yeast extract. The pH was adjusted to 7.5 and 100-150 mg sodium dithionite were added to reduce as much oxygen as possible.

DNA Isolation and DGGE Analysis

DNA was isolated from bacterial cell pellets using the PowerWater® DNA Isolation kit according to manufacturer instructions with the following exceptions: (1) Samples were not filtered. Instead, cell pellets were resuspended in 1 mL Solution PW1 and then transferred to PowerWater® Bead Tubes. (2) DNA was eluted from the Spin Filter with 50 µL of Solution PW6. DNA fragments were amplified for DGGE analysis from the 16S rRNA genes for each sample. This was performed using the PCR primers described in Table 1, the PCR reaction mix described in Table 2 and the thermal cycling conditions described in Table 3. DGGE analysis was then performed on the resulting DNA fragments according to Schafer and Muyzer method described in Schafer, H.; Muyzer, G. "Denaturing Gradient Gel Electrophoresis in Marine Microbial Ecology" In *Methods in Microbiology*; John Paul, Ed; Academic Press: London, 2001; pp 425-468.

TABLE 1

PCR primers

| Primer | Sequence (5'-3') |
|---|---|
| Bac342 + GC | SEQ ID NO: 1 CGCCCGCCGCGCCCCGCGCCCGTCCCGCCGCCCCGCC CGCCTACGGGAGGCAGCAG |
| Bac907rM | SEQ ID NO: 2 CCGTCAATTCMTTTGAGTTT* |

*Degenerate primer that contains either A or C at position indicated with "M"

TABLE 2

PCR reaction mix for the amplification of 16S rRNA gene fragments for DGGE analysis

| Component | Amount | Details |
|---|---|---|
| Mastermix | 25 µL | HotStarTaq Mastermix kit; Qiagen |
| Forward Primer | 0.3 µL of 50 µM stock | Bac342 + GC; Integrated DNA Technologies |
| Reverse Primer | 0.3 µL of 50 µM stock | Bac907rM; Integrated DNA Technologies |
| Microbial DNA-free water | 23.4 µL | Qiagen |
| Template DNA | 1 µL | Genomic DNA isolated from sample cell pellets |

TABLE 3

Thermal cycling conditions for the amplification of the 16S rRNA gene fragment

| Step | Temperature (° C.) | Time (min) |
|---|---|---|
| 1 | 95 | 15:00 |
| 2 | 95 | 0:30 |
| 3 | 65 | 0:30 |
| 4 | 72 | 1:00 |
| 5 | Repeat steps 2 through 4 for 19 additional cycles, decreasing the temperature in step 3 by 0.5° C. each cycle | |
| 6 | 95 | 0:30 |
| 7 | 55 | 0:30 |
| 8 | 72 | 1:00 |
| 9 | Repeat steps 6 through 8 for 13 additional cycles | |
| 10 | 72 | 15:00 |

Challenge of SRB cultures with *Brassicibacter mesophilus*

A 25 mL culture of each of the SRB challenged was grown for 4 days. Cultures were then split equally 5 ways into clean serum vials. The 5 culture aliquots (each 5 mL) were treated as described in Table 4.

TABLE 4

Treatment conditions for SRB challenge

| Sample label | Treatment condition |
|---|---|
| Untreated | No treatment |
| Loop 1 culture | Added 100 µL of culture collected from Loop 1 |
| Loop 1 spent media | Added 100 µL of spent media collected from Loop 1 |
| Loop 2 culture | Added 100 µL of culture collected from Loop 2 |
| Loop 2 spent media | Added 100 µL of spent media collected from Loop 2 |

After treatment, cultures incubated at 30° C. under anaerobic conditions. 1 mL samples were taken from each culture at specified time points. Samples were immediately centrifuged at 16000×g for 5 min. The resulting supernatant was discarded and pellets were frozen at −80° C. until pellets were thawed for DNA isolation.

Results of Challenge of *D. vulgaris* with *B. mesophilus*

*D. vulgaris* culture was challenged with the culture from two separate contaminated loop setups. Both of these cultures have been previously shown to contain *B. mesophilus* as the only component by DGGE analysis. To investigate the possibility that *B. mesophilus* is affecting *D. vulgaris* growth through the secretion of metabolites or enzymes into the surrounding media, spent media was also prepared from the *B. mesophilus* cultures and tested for its effect on *D. vulgaris* growth. Treated and untreated *D. vulgaris* culture samples were taken prior to treatment and 3, 5 and 13 days post-treatment and evaluated for microbial composition by DGGE analysis (Table 5).

TABLE 5

Challenge of SRBs with *Brassicibacter mesophilus*

| Lane | SRB culture treatment conditions | Growth time | Relative intensity of SRB band | Relative intensity of *B. mesophilus* band |
|---|---|---|---|---|
| | | *D. vulgaris* | | |
| 1 | Untreated | 0 days | 1.0 | |
| 2 | | 3 days | 2.6 | |
| 3 | | 5 days | 3.7 | |
| 4 | | 13 days | 4.2 | |
| 5 | *B. mesophilus* culture 1 | 3 days | 4.4 | 0.1 |
| 6 | | 5 days | 5.2 | 0.3 |
| 7 | | 13 days | 1.2 | 4.3 |

TABLE 5-continued

Challenge of SRBs with *Brassicibacter mesophilus*

| Lane | SRB culture treatment conditions | Growth time | Relative intensity of SRB band | Relative intensity of *B. mesophilus* band |
|---|---|---|---|---|
| 8 | Spent media from *B. mesophilus* culture 1 | 3 days | 5.0 | |
| 9 | | 5 days | 5.4 | |
| 10 | | 13 days | 5.8 | |
| 11 | *B. mesophilus* culture 2 | 3 days | 2.4 | |
| 12 | | 5 days | 2.0 | |
| 13 | | 13 days | 1.4 | 2.4 |
| 14 | Spent media from *B. mesophilus* culture 2 | 3 days | 2.4 | |
| 15 | | 5 days | 1.4 | |
| 16 | | 13 days | 2.7 | |
| *D. alaskensis* | | | | |
| 1 | Untreated | 0 days | 1.0 | |
| 2 | | 3 days | 1.6 | |
| 3 | | 5 days | 0.9 | |
| 4 | | 13 days | 0.3 | |
| 5 | *B. mesophilus* culture 1 | 3 days | 0.2 | 0.0 |
| 6 | | 5 days | 0.9 | 0.1 |
| 7 | | 13 days | 0.5 | 1.2 |
| 8 | Spent media from *B. mesophilus* culture 1 | 3 days | 1.0 | |
| 9 | | 5 days | 0.8 | |
| 10 | | 13 days | 1.2 | |
| 11 | *B. mesophilus* culture 2 | 3 days | 1.1 | 0.1 |
| 12 | | 5 days | 0.5 | 0.9 |
| 13 | | 13 days | 0.5 | 1.1 |
| 15 | Spent media from *B. mesophilus* culture 2 | 5 days | 1.0 | |
| 16 | | 13 days | 0.9 | |

Qualitative examination of the DGGE gel revealed that treatment of *D. vulgaris* culture with Loop 1 culture resulted in a dramatic decrease in band intensity for lower bands in lanes 5-7. The most probable cause for these lower levels of *D. vulgaris* DNA is a decrease in the density of *D. vulgaris* cells in the culture. In contrast, bands corresponding to *B. mesophilus* DNA in these same samples increased over the course of the experiment. This indicates that the growth of *B. mesophilus* in the mixed culture negatively impacted *D. vulgaris* viability. Loop 2 culture appeared to have a less dramatic effect of *D. vulgaris* growth; however, analysis of band intensity by densitometry indicated that the band corresponding to *D. vulgaris* DNA did decrease by 42% over the course of the experiment. This is in contrast to the 162% increase in band intensity observed for untreated *D. vulgaris*. Thus, while the effect of *B. mesophilus* on *D. vulgaris* was less dramatic in cultures inoculated with Loop 2 culture than those inoculated with Loop 1 culture, a negative effect on *D. vulgaris* growth was observed in the presence of both cultures containing *B. mesophilus*. In contrast, the addition of spent media from Loop 1 and Loop 2 culture to *D. vulgaris* had little impact on *D. vulgaris* growth.

Challenge of other *Desulfovibrio* strains with *B. mesophilus*

To evaluate the generality of the effect observed for *B. mesophilus*, this organism was co-cultured with other organisms from the *Desulfovibrio* genus. In particular, cultures of *Desulfovibrio alaskensis* were each treated with either flow loop culture or spent media from flow loop culture. As described above for *D. vulgaris*, treated and untreated culture samples were taken prior to treatment and 3, 5 and 13 days post-treatment and evaluated by DGGE analysis (Table 5).

Examination of the DGGE gel for *D. alaskensis* revealed many more bands than were observed in the DGGE gel for the challenge experiments involving *D. vulgaris*. To facilitate analysis, the bands were excised from the gel. DNA was eluted from the gel slices and submitted for sequencing to provide more information about the organisms that were represented by each band. The length of the DNA fragments extracted was only 580 bp; this size fragment was insufficient to provide a sequence length that will allow the species of bacteria represented by each band to be determined. However, this sequence length was sufficient to determine the genus of bacteria represented by each band, and the results of this analysis are summarized in Table 6. This evaluation revealed the presence of multiple organisms in the cultures extracted from Loops 1 and 2. Other than *B. mesophilus*, these cultures contained *Bacillus*, *Paenibacillus*, and another organism that could not be identified.

TABLE 6

Sequencing analysis of *D. alaskensis* DGGE bands

| Band | Genus | Sequence match (%) |
|---|---|---|
| 1 | inconclusive | |
| 2 | *Bacillus* | 99 |
| 3 | *Brassicibacter* | 99 |
| 4 | *Brassicibacter* | 99 |
| 5 | *Paenibacillus* | 99 |
| 6 | *Desulfovibrio* | 99 |

Regardless of the additional organisms present, it does appear that the bands corresponding to *D. alaskensis* decreased in intensity in samples isolated from culture incubated with Loop 1 and Loop 2 cultures. Incubation of *D. alaskensis* with Loop 1 culture resulted in a 29% decrease in *D. alaskensis* band intensity over the course of the experiment and incubation of *D. alaskensis* with Loop 2 culture resulted in a 55% decrease in band intensity.

What is claimed is:

1. A method of controlling the growth of a sulfate reducing bacteria in an aqueous system comprising
introducing *Brassicibacter mesophilus* to the aqueous system at suitable conditions allowing growth of said *B. mesophilus* in the system, wherein an increase in the growth of *Brassicibacter mesophilus* inhibits growth of sulfate reducing bacteria of the genus *Desulfovibrio* in the system.

2. The method of claim 1 wherein the sulfate reducing bacteria is *Desulfovibrio vulgaris*.

3. The method of claim 1, which is a batch method, whereby the aqueous system is contacted once with the *Brassicibacter mesophilus*.

4. The method of claim 1, which is a continuous method, whereby the *Brassicibacter mesophilus* is repeatedly introduced into the aqueous system.

5. The method of claim 1, wherein the aqueous system is contaminated with said sulfate-reducing bacteria after introduction of *Brassicibacter mesophilus* and wherein the presence of *B. mesophilus* in the system inhibits the growth of said sulfate reducing bacteria.

6. The method of claim 1, wherein the aqueous system is a potable aqueous system, wastewater or an industrial aqueous system.

7. A method of controlling the growth of a sulfate reducing bacteria in aqueous systems involved in oil and gas production and transportation comprising
introducing *Brassicibacter mesophilus* to the aqueous system at suitable conditions allowing growth of said *B. mesophilus* in the system, wherein an increase in the growth of *Brassicibacter mesophilus* inhibits growth of sulfate reducing bacteria of the genus *Desulfovibrio* in the system.

8. The method of claim 7, wherein said aqueous system into which *B. mesophilus* is introduced and growing is water that is injected into a subterranean oil-bearing formation during oil recovery.

\* \* \* \* \*

SEQUENCE LISTING

<160> NUMBER OF SEQ ID NOS: 2

<210> SEQ ID NO 1
<211> LENGTH: 57
<212> TYPE: DNA
<213> ORGANISM: Artificial Sequence
<220> FEATURE:
<223> OTHER INFORMATION: Synthetic primer sequence

<400> SEQUENCE: 1
cgcccgccgc gccccgcgcc cgtcccgccg ccccccgcccg cctacgggag gcagcag        57

<210> SEQ ID NO 2
<211> LENGTH: 20
<212> TYPE: DNA
<213> ORGANISM: Artificial Sequence
<220> FEATURE:
<223> OTHER INFORMATION: Synthetic primer sequence

<400> SEQUENCE: 2
ccgtcaattc mtttgagttt        20